United States Patent [19]

Liapis et al.

[11] Patent Number: 4,874,524

[45] Date of Patent: Oct. 17, 1989

[54] SEPARATION OF ADSORBED COMPONENTS BY VARIABLE TEMPERATURE DESORPTION

[75] Inventors: Athanasios I. Liapis; Marshall E. Findley, both of Rolla, Mo.; Hoa T. Nguyen, San Jose, Calif.

[73] Assignee: The Curators of the University of Missouri, Columbia, Mo.

[21] Appl. No.: 175,329

[22] Filed: Mar. 30, 1988

[51] Int. Cl.$^4$ .................. B01D 15/08; B01D 53/04
[52] U.S. Cl. ........................ 210/672; 55/31; 55/59; 55/62; 55/73; 55/74; 55/75; 203/41; 210/673; 585/825
[58] Field of Search ............. 55/31, 59, 62, 73–75; 210/672, 673, 656–659; 585/825; 203/41

[56] References Cited

U.S. PATENT DOCUMENTS 1,906,917  5/1933  Peters et al. ........................ 55/66
3,080,433  3/1963  Hengstebeck ..................... 585/825

*Primary Examiner*—Ivars Cintins
*Attorney, Agent, or Firm*—Senniger, Powers, Leavitt and Roedel

[57] ABSTRACT

An adsorption-desorption process for separation of a component from a feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising charging the feed mixture to an inlet end of a bed of the adsorbent material, passing the feed mixture through the bed under such conditions that the adsorbent material adsorbs said first and second components of the feed mixture, withdrawing an effluent from an outlet end of the bed, the effluent consisting essentially of feed mixture decreased in content of the materials adsorbed by the bed, after the adsorbent material is substantially saturated, desorbing the first and second components from the adsorbent material in at least two steps at substantially the same pressure but at different temperatures, the temperature of the first desorption step being less than the temperature of a subsequent desorption step, and separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

20 Claims, No Drawings

SEPARATION OF ADSORBED COMPONENTS BY VARIABLE TEMPERATURE DESORPTION

BACKGROUND OF THE INVENTION

This invention relates generally to the separation of components from a feed stream through the use of adsorption and desorption and more particularly to the provision of such a process wherein desorption is carried out in multiple steps at different temperatures to improve the separation of the components.

Adsorption has been used to remove small amounts of impurities or small quantities of valuable products from liquids or gases and to remove and recover solvents from air used in solvent drying. Adsorption has been proposed, but not extensively used for high volume products primarily because the use of solids makes it more difficult and complex to use continuous processes and multiple stages. Unless an almost complete separation can be obtained in one stage, adsorption is often an unfavorable process.

In a typical adsorption-desorption separation process, a feed stream of the mixture is charged to the inlet of a fixed bed of adsorbent material which preferentially adsorbs one of the components of the mixture that is present, usually a component with a small concentration. The feed stream passes through the bed and the effluent is withdrawn from the outlet of the bed, the effluent having a decreased content of those components that have been adsorbed by the bed. The process continues until the adsorbent is substantially saturated and then, the bed is regenerated.

A method of previously employed to regenerate the bed comprises passing hot regeneration gases through the bed of adsorbent material, either in the direction of flow of the feed, or in the opposite direction of the feed. See, e.g., Hengstebeck, U.S. Pat. No. 3,080,433. Alternatively, desorption has been carried out in one step by lowering the pressure, by passing a gas or vapor containing a minimum of the adsorbed components over the bed of absorbent, by heating to a high temperature, or by a combination of these methods.

Where desorption is carried out in one step, and more than one component is adsorbed, all of the adsorbed components are removed together. Accordingly, the desorbed material has the same amounts of each component as existed in the adsorbed state on the adsorbent and the desired separation may not be obtained with one step of desorption. However, if desorption could be carried out in multiple steps, with one or more of the adsorbed components being preferentially desorbed in a first step and one or more of the remaining adsorbed components preferentially desorbed in a subsequent step, greater separation could be achieved. Such further separation would clearly increase the economies of adsorption as a means for separation.

SUMMARY OF THE INVENTION

Among the objects of the invention, therefore, may be noted the provision of a process for multiple steps desorption to achieve greater separation than for single step desorption where two or more components are adsorbed; the provision of such a process that selectively removes a higher concentration of a component in a first desorption step than in a subsequent desorption step and a higher concentration of at least one other component in a subsequent desorption step than in the first step; the provision of such a process wherein the desorbed streams from each step are separately recovered according to the high concentration component, resulting in an increased separation in the desorption stage of the overall separation process.

Briefly, therefore, the present invention is directed to an adsorption-desorption process for separation of a component from a feed mixture of components wherein at least two components of the feed mixture are adsorbed by an adsorbent material during the adsorption step of the adsorption-desorption process and the adsorbent material has a greater affinity for a first one of the adsorbed components than for a second one of the adsorbed components. The process comprises charging the feed mixture to an inlet end of a bed of the adsorbent material, passing the feed mixture through the bed under such conditions that the adsorbent material adsorbs the first and second components of the feed mixture, and withdrawing an effluent from an outlet end of the bed, the effluent consisting essentially of feed material decreased in content of the materials adsorbed by the bed. After the adsorbent material is substantially saturated, the first and second components are desorbed from the adsorbent material in at least two steps at substantially the same pressure but at different temperatures, the temperature of the first desorption step being less than the temperature of a subsequent desorption step. The material desorbed in the two steps is separately recovered, with the concentration of the first component being greater in the material recovered from the subsequent desorption step than in the material recovered from the first desorption step, and the concentration of the second component being greater in the material recovered from the first desorption step than in the material recovered from the subsequent desorption step.

In an alternative embodiment, the first and second components are desorbed into a stripper gas during the desorption stage of the adsorption-desorption process of the present invention. As in the previous embodiment, desorption into the stripper gas is carried out in at least two steps at different temperatures, the temperature of the first desorption step being less than the temperature of a subsequent desorption step. Also, the material desorbed in the two steps is separately recovered, with the concentration of the first component being greater in the material recovered from the subsequent desorption step than in the material recovered from the first desorption step, and the concentration of the second component being greater in the material recovered from the first desorption step than in the material recovered from the subsequent desorption step.

The present invention is additionally directed to a process for the separation of ethanol from an ethanol-water mixture comprising about 2 to about 50% ethanol by weight. The process comprises charging the feed ethanol-water mixture to an inlet end of a bed of adsorbent material having a greater affinity for ethanol than for water, passing the feed mixture through the bed, and withdrawing an effluent from an outlet end of the bed, the effluent consisting esssentially of feed material decreased in content of the ethanol and water adsorbed by the bed. After the adsorbent material is substantially saturated, the ethanol and water are desorbed with a flow of stripper gas from the adsorbent material in at least two steps at substantially the same pressure but at different temperatures, one of the steps being carried out at a temperature of about 45° C. to about 95° C. and a subsequent desorption step being carried out at a greater temperature than that of the first step, the temperature of the second step being about 75° C. to about 150° C. The material desorbed in the two steps is separately recovered with the concentration of water being greater in the material recovered from the first desorption step than in the material recovered from the subsequent desorption step and the concentration of ethanol being greater in the material recovered from the subsequent desorption step than in the material recovered from the first desorption step.

Other objects and features will be in part apparent and in part pointed out hereinafter.

DESCRIPTION OF THE PREFERRED EMBODIMENTS

In accordance with the present invention, a novel process has been discovered which improves the separation of components over heretofore available adsorption-desorption processes. This invention is uniquely adapted for the separation of one or more components from multicomponent mixtures such as ethanol-water, carbon dioxide-hydrogen sulfide-hydrocarbon, styrene-ethylbenzene, and propylene-propane, where more than one component is adsorbed on the adsorbent employed.

In conventional adsorption-desorption separation processes, the separation occurs during adsorption. After the adsorbent material has substantially saturated, the adsorbent bed is regenerated and the adsorbed material removed in a single stream. However, it has surprisingly been discovered that where more than one component is adsorbed, the separation can be substantially improved if the adsorbed material is desorbed in steps, the first desorption step being carried out at a lesser temperature than later desorption steps. Such variable temperature, multi-step desorption results in the preferential desorption of one component from the adsorbent in the first desorption step relative to subsequent desorption steps and the preferential desorption of the remaining component(s) from the adsorbent in subsequent desorption steps relative to the first desorption step. Thus, additional separation is achieved over conventional adsorption-desorption processes where the adsorbed phase is desorbed in one step.

The adsorption step of the present invention is similar to conventional adsorption processes. The feed mixture is charged to the bed of adsorbent material until the adsorbent material is substantially saturated. As used herein, a bed is considered to be substantially saturated if the capacity of the adsorbent material is nearly exhausted, or if the passage of any further feed material will result in the breakthrough of an offending component. However, after the adsorbent material is substantially saturated, the bed is regenerated in accordance with the present invention in a novel manner that results in increased separation.

The process of the present invention has application where the adsorbent material adsorbs at least two components of the mixture to be separated and preferentially adsorbs one of the components (to be separated from the mixture) over the other adsorbed component(s) of the mixture. Preferably, the difference in adsorptivities of the adsorbent with respect to the adsorbed components is as great as possible and at least about 10 percent. Most preferably, the difference in adsorptivities is at least about 50 percent. To some extent, the relative affinities of an adsorbent material for components of a mixture may be predicted from the affinity of the adsorbent material for each of the components in their pure states. However, because the affinity of an adsorbent material for a component in its pure state may differ from its affinity for that component when present in a mixture, the relative affinities of the adsorbent material for each of the components in their pure state should only be used as a starting point in selecting an adsorbent material for use in accordance with this invention. In some cases, it may be necessary to evaluate the particular adsorbent material using a sample of the mixture to be separated.

Preferably, the affinity of the adsorbent material for the components adsorbed from the feed mixture also changes with temperature. That is, the greater the change in adsorptivity with temperature, the more likely it is that variable temperature desorption in accordance with the invention will give additional separation over one step desorption.

The adsorptivity of the adsorbent material for the component to be preferentially adsorbed should be as great as practically possible and in most instances should be at least about 1% by weight of the adsorbent, preferably at least about 5% by weight of the adsorbent, and most preferably at least about 10% by weight of the adsorbent. However, if the preferentially adsorbed component is too strongly adsorbed, desorption may become economically unfavorable. Thus, in some cases it may not be economically practical to use an adsorbent material having the greatest affinity for the component to be preferentially adsorbed.

Similar to conventional adsorption processes, it is preferred that the adsorbent material preferentially absorb the low concentration component of the mixture to be separated. This reduces the frequency with which the adsorbent material must be regenerated. For instance, activated charcoal is preferred as the adosrbent for the separation of ethanol from ethanol-water mixtures comprising about 5 to about 50 percent by weight ethanol. Alternatively, molecular sieves, silica gel, alumina, dessicants and carbohydrates such as starch are preferred as the adsorbent for the separation of water from ethanol-water mixtures comprising about 50 to about 99 percent by weight ethanol.

The desorption steps of the present invention are carried out at different temperatures (or different temperature ranges), with the temperature of each subsequent desorption step being greater than the temperature of the preceding step. Preferably, the temperature of the first desorption step is above the adsorption temperature but is as low as possible to maximize the selective desorption of the weakly adsorbed components. This follows from the fact that for physically adsorbed components, desorption from a solid adsorbent into either a gas or liquid phase is increased by both rate and equilibrium effects as temperature is increased, and in addition, weakly adsorbed components will generally desorb at lower temperatures than strongly adsorbed components. Such effects can be more important than vapor pressures or solubilities of the pure components. Rates, equilibrium effects and heats of desorption are important in variable temperature desorption and determine the appropriate temperatures to be used. The temperature of the last desorption step is that temperature at which desorption is complete but not greater than that temperature which would affect the stability of the adsorbed components or the adsorbent.

Significantly, a single desorption step of the present invention may comprise desorption over a range of temperatures. For instance, in the desorption of water and ethanol from activated charcoal, the first desorption step may comprise desorption from 45° C. to 90° C., whereas the second desorption step may comprise desorption from 90° C. to 140° C. Alternatively, the ethanol and water may be desorbed in more than two steps, e.g., a first step comprising desorption from 45° C. to 75° C., a second step comprising desorption from 75° C. to 105° C. and a third step comprising desorption from 105° C. to 140° C. The number of desired desorption steps (in excess of two) for any one process will depend, in part, upon the number of components adsorbed during the adsorption step and the desired purity of the desorbed components.

Preferably, the pressure is substantially the same for each desorption step of the invention and most preferably, the pressure is atmospheric. Employing substantially the same pressure for each desorption step, in general, and atmospheric pressure, in particular, offers significant cost advantages over variable pressure desorption.

The present invention has particular application as a separation technique for components that are difficult to separate economically by distillation, such as ethanol-water mixtures comprising less than 50% by weight ethanol, in general, and ethanol-water mixtures from fermentations which generally produce a 6% to 12% by weight ethanol product. In such cases (as demonstrated in the below Examples), activated carbon can be used to preferentially adsorb ethanol from solutions of about 6% by weight ethanol at a temperature of about 40° C. However, some water is also adsorbed and the resulting adsorbed phase is approximately 40% by weight ethanol and 60% by weight water. By the use of multi-step variable temperature desorption at atmospheric pressure, most of the water can be desorbed into an air stream at temperatures up to and including 90° C., and later condensed to give a condensate of about 5% ethanol. At temperatures from about 90° C. to 140° C., most of the ethanol can be desorbed into an air stream at atmospheric pressure and then condensed to give a 91% by weight ethanol product instead of the approximately 40% ethanol product that would result from complete desorption in one step.

The same type of separation can be produced with different ethanol-water feed compositions, and different temperatures of adsorption and desorption would result in differing product compositions but similar separations. Pressures other than atmospheric (with different temperatures of desorption) could also be used to give similar results.

Alternatively, to remove water from an ethanol-water solution of more than about 50% ethanol, a dessicant adsorbent such as silica gel, alumina, molecular sieves, or certain carbohydrates like cellulose or starch can be used. And if such an adsorbent adsorbed significant amounts of ethanol as well as water, then variable temperature desorption would be useful to remove ethanol from the adsorbent at low temperatures followed by higher temperature regeneration by complete drying.

Additionally, this invention could be utilized in many multicomponent adsorption processes such as carbon dioxide-hydrogen sulfide-natural gas, styrene-ethylbenzene, and propylene-propane systems where the adsorbed components are desorbed as a gas. Likewise, this invention is also suited to the desorption of adsorbed components into a liquid stream.

In processes where it is desired to separate a component from a mixture and that component is adsorbed by the adsorbent material along with two or more other components of the feed mixture, the adsorbent material preferably has a greater affinity for the component to be separated than it does for at least one of the other adsorbed components. Most preferably, the adsorbent material has a greater affinity for the component to be separated than for each of the other adsorbed components. In accordance with the present invention, therefore, desorption may be carried out in two or more steps with the concentration of one or more of the other components in the adsorbed phase being greater in the material recovered from a first desorption step than in a subsequent desorption step (which is carried out at a greater temperature than that at which the first desorption step is carried out) and the concentration of the component to be separated being greater in the subsequent desorption step than the first desorption step.

The terms first and subsequent as used herein in connection with desorption steps are not used in a limiting sense and thus, are used to denote only the "first" and "subsequent" of those two desorption steps. For instance, where desorption is carried out in four steps, the "first" and "subsequent" desorption steps could be the third and fourth desorption steps, the second and fourth desorption steps, etc. In accordance with the present invention, however, the "subsequent" desorption step is carried out at a greater temperature than is the "first" desorption step.

The thermal changes necessary to effect variable temperature desorption can be used with presently available, conventional equipment. Depending upon the particular adsorbed component, it may be preferable to employ a stripper gas, preferably air or an inert gas, at the desired temperature or alternatively through the use of a thermal wave or by heating of the entire column simultaneously.

This process invention provides for increased separation in one stage of adsorption-desorption and increased relative concentrations of desorbed components after desorption. This advantage can be very important in applying adsorption methods to new applications where adsorption was previously not very practical. In addition, the potential application of better desorption methods may allow processes which were previously unfeasible due to separation costs to become more feasible.

The following examples illustrate the invention.

EXAMPLE 1

SEPARATION OF ETHANOL FROM A WATER ETHANOL MIXTURE

Table I provides data on the adsorption of pure ethanol and pure water on activated carbon previously regenerated with air at 160° C. and 1 Atm pressure. To generate this data, air and vapor were circulated and in equilibrium with pure liquid at 40° C. Desorption was into air, circulated through a condenser at 25° C. Table I also provides the amount desorbed at various temperatures. Both types of data indicate adsorption followed by variable temperature desorption is a promising separation method for ethanol-water mixtures using activated charcoal.

Ethanol and water were vaporized into a recirculating stream *of air from a flask containing* 6% by weight ethanol in water in a water bath at 40° C. The air-water-ethanol gas mixture was pumped through an adsorption column containing activated carbon (CALGON F 200) with the column in a hot water bath at 45° C. The column had been previously used with water and ethanol and then desorbed at 100° C. From the column, the air stream was recirculated to the flask. The column was kept at a temperature greater than that of the the ethanol-water solution to prevent condensation in the adsorbent bed.

After 2 to 3 hours of recirculation, the weight of the column was approximately constant indicating that adsorption was complete, and approximately at equilibrium with the air stream. The composition of the adsorbed components was approximately 40% by weight ethanol (see Total Desorbed in Table II). This is a significant increase in ethanol concentration but not a nearly complete separation.

The adsorbed material was then desorbed by pumping air through the adsorption column to a condenser with 25° C. cooling water circulating therein, and then to a container where the condensed liquid was removed and the air stream recirculated to the pump. The water bath around the adsorption column was gradually increased in temperature by a heater, and the outlet air temperature from the adsorbent was measured. The condensate collected was periodically removed, weighed, and analyzed by gas chromatography to obtain the results in Table II.

The total condensate collected up to 63° C. had a concentration of 15.8% ethanol, while the condensate collected from 63° C. to 73° C. had a concentration of 92% ethanol, a very significant increase from the approximately 40% ethanol concentration of the adsorbed components. If the 15.8% ethanol were too high for a practical separation, the intermediate portions from about 52° C. to 63° C. could be recycled to the next adsorption cycle. In this case 73% of the ethanol desorbed was desorbed at temperatures from 63° C. to 73° C., while almost 96% of the water desorbed was desorbed in the temperature range from 51° C. to 63° C.

The data in Table III were collected in a similar way except that during desorption the column of activated carbon was immersed in an oil bath. The carbon had been previously used and desorbed at 140° C. The adsorption was carried out at 44° C. instead of 45° C., and during desorption the oil bath temperature was measured instead of the outlet gas temperature. In the test for Table III data, the adsorbed components had a concentration of about 29 weight % ethanol (from total amount desorbed). The variable temperature desorption for Table III was carried out more rapidly than in the run for Table II. Primarily water was desorbed at temperatures up to 90° C., with 96% of the water in the condensate collected at adsorbent bath temperatures from 50° C. to 90° C. The ethanol concentration in all the condensate up to 90° C. was 4.7%, and at temperatures from 90° C. to 140° C. the total condensate was 91.1% ethanol, and this condensate included 88% of the total ethanol than was desorbed.

In both Table II and Table III, the charcoal used had already been through several cycles of adsorption and desorption with ethanol and water.

TABLE I

ADSORPTION AND DESORPTION DATA ON PURE WATER AND PURE ETHANOL ADSORPTION FROM AIR AND VAPOR AT 45° C.

|  | Total Amount Adsorbed g/g A.C. | Desorbed at 60° C. g/g A.C. | Desorbed 60° C. to 90° C. g/g A.C. | Desorbed 90° C. to 120° C. g/g A.C. | Desorbed 120° C. to 160° C. g/g A.C. |
|---|---|---|---|---|---|
| Water | .234 | .0702 | .0488 | .0668 | .0485 |
| Ethanol | .479 | .1721 | .1869 | .0960 | .0245 |
|  |  | PERCENT DESORBED | | | |
| Water |  | 30 | 21 | 28 | 21 |
| Ethanol |  | 36 | 39 | 20 | 5 |

TABLE II

Data on desorption of activated carbon with adsorbed ethanol and water per gram of activated carbon. Ethanol and Water were previously adsorbed from air and vapor at 45° C. Air and vapor were in equilibrium with 6 wt % ethanol in water solution at 40° C.

|  | TOTAL WEIGHT per Act. C. | WT FRACT. ETHANOL | WT ETHANOL per g Act. C. | WT H$_2$0 per g Act. C. |
|---|---|---|---|---|
| Desorbed* Outlet Temp = 51° C. | .0343 | .073 | .0025 | .0318 |
| Desorbed T = 51 to 52 | .0195 | .182 | .0035 | .0160 |
| Desorbed T = 52 | .0025 | .182 | .0005 | .0020 |
| Desorbed T = 52 to 60 | .0013 | .344 | .0004 | .0009 |
| Desorbed T = 60 to 61 | 0017 | .276 | .0005 | .0012 |
| Desorbed T = 61 | .0016 | .293 | .0005 | .0011 |
| Desorbed T = 61 | .0023 | .46 | .0011 | .0012 |
| Desorbed T = 61 | .0010 | .46 | .0005 | .0005 |
| Desorbed T = 61 to 63 | .0016 | .56 | .0009 | .0007 |
| Total to 63° C. | .0658 | .158 | .0104 | .0554 |
| Desorbed Outlet T = 63 to 67 | .0032 | .76 | .0024 | .0008 |
| Desorbed T = 63 to 72 | .0075 | .90 | .0068 | .0007 |
| Desorbed T = 72 | .0105 | .97 | .0102 | .0003 |
| Desorbed T = 72 to 73 | .0049 | .95 | .0047 | .0002 |
| Desorbed T = 73 | .0012 | .95 | .0011 | .0001 |
| Desorbed T = 73 | .0013 | .95 | .0012 | .0001 |
| Desorbed T = 73 | .0020 | .92 | .0018 | .0002 |
| Total 63 to 73° C. | .0306 | .92 | .0282 | .0024 |
| Total Desorbed* | .0964 | .4 | .0386 | .0578 |

*Desorption probably incomplete. Desorbed into an air stream and condensed at about 25° C. with air stream recirculated to activated carbon column.

TABLE III

Data on desorption of activated carbon with adsorbed ethanol and water per gram activated carbon. Ethanol and water were previously adsorbed from air and vapor at 44° C. Air and vapor were in equilibrium with 6 wt % of ethanol in water solution at 40° C.

| TOTAL | WEIGHT DESORBED (g/g A.C.) | WT FRACT. ETHANOL | WT ETHANOL (g/g A.C.) | WT $H_2O$ (g/g A.C.) |
|---|---|---|---|---|
| Desorbed 50° C.* Bath Temp. | .0505 | .006 | .0003 | .0502 |
| Desorbed 50° to 60° C. | .0447 | .047 | .0021 | .0426 |
| Desorbed 60° to 70° C. | .0100 | .110 | .0011 | .0089 |
| Desorbed 70° to 80° C. | .0029 | .138 | .0004 | .0025 |
| Desorbed 80° to 90° C. | .0044 | .318 | .0014 | .0031 |
| Total Desorbed to 90° C. | .1125 | .047 | .0053 | .1073 |
| Desorbed 90° to 100° C. | .0043 | .581 | .0025 | .0018 |
| Desorbed 100° to 140° C. | .0395 | .947 | .0374 | .0021 |
| Total Desorbed 90° to 140° C. | .0438 | .911 | .0399 | .0039 |
| Total Desorbed | .1563 | .289 | .0452 | .1112 |

*Desorbed into an air stream and condensed at about 25° C. with air recirculated to activated carbon column.

EXAMPLE 2

SEPARATION OF STYRENE AND ETHYLBENZENE FROM A STYRENE-ETHYLBENZENE MIXTURE

The data in Table IV were obtained in a similar manner as that for Table I except that styrene and ethylbenzene were studied. Calgon F-200 activated carbon was used.

Although there is not much difference between the adsorption of *styrene and ethylbenzene,* there appears to be a tendency for ethylbenzene to desorb at lower temperatures and thus some separation by variable temperature desorption of this invention was expected.

Table V shows data obtained by adsorption and desorption starting with 49.5% styrene, 50.5% ethylbenzene (by weight) liquid solution at 55° C. A nitrogen stream picked up styrene and ethylbenzene vapor from the liquid solution at equilibrium and was pumped through a column of activated carbon at 60° C. The $N_2$ was then recirculated to liquid solution for about 3 hours.

The column was then desorbed into a nitrogen stream at various temperatures that was recirculated through a condenser at approximately 23° C., and the condensate was collected at the various temperatures, and analyzed with a gas chromatograph. The results are shown in Table V.

Table V shows that some separation has been achieved by adsorption, with the total amount desorbed at 54% compared to 49.5% original concentration of styrene. Some additional separation is achieved by variable temperature desorption to reach a concentration of almost 56% styrene from the higher temperature desorption. This is probably not an ideal separation method, but, styrene and ethylbenzene are also very difficult and costly to separate by other methods such as distillation. Thus, modifications of this technique at different conditions or more selective adsorbents could improve this method.

TABLE IV

| | Adsorbed* g/g Act. C. | Desorbed** g/g Act. C. at | | | |
|---|---|---|---|---|---|
| | | 60° C. | 90° C. | 120° C. | 160° C. |
| Pure Styrene | 0.504 | .231 | .133 | 0.062 | .078 |
| Pure Ethylbenzene | 0.475 | .322 | .043 | 0.040 | .070 |

*From $N_2$ and vapor at 60° C., $N_2$ and vapor in equilibrium with liquid at 55° C. Act. C. previously desorbed at 160° C. Measured by amount desorbed.
**Into $N_2$ circulated from Act. C. to condenser at 23° C. and back to Act. C.

TABLE V

| | Weight Desorbed g/g Act. C. | Weight Fract. Styrene | Styrene Desorbed g/g Act. C. | Ehtylbenene desorbed g/g Act. C. |
|---|---|---|---|---|
| Desorbed at 60° C. | .168 | .515 | .087 | .081 |
| Desorbed at 90° C. | .071 | .553 | .039 | .032 |
| Desorbed at 120° C. | .055 | .558 | .031 | .024 |
| Desorbed at 160° C. | .093 | .562 | .052 | .041 |
| Total Desorbed 60° C. to 160° C. | .219 | .557 | .122 | .097 |
| Total Desorbed | 0.387 | .540 | .209 | .178 |

EXAMPLE 3

SEPARATION OF PROPYLENE AND PROPANE FROM A PROPYLENE—PROPANE MIXTURE

Table VI presents data obtained on the adsorption and desorption of pure propane and pure propylene on molecular sieves 5A obtained from Union Carbide. In both cases the pure gases were adsorbed onto a column of molecular sieves that had previously been used for adsorption of these gases and had been desorbed at 160° C. and 1 atmosphere pressure. The adsorbent and gas were allowed to equilibrate at 27° C., after which they were desorbed at various temperatures up to 160° C. The amount adsorbed was determined by the total amount desorbed.

Table VI also shows the adsorptivity of pure propane and a pure propylene on molecular sieves 5A as published by Union Carbide, the manufacturer of the sieves used. The difference in adsorptivity is believed to be due to the fact that the molecular sieves were not completely desorbed prior to determining the amount adsorbed and desorbed. This was partially in order to simulate industrial adsorption cycles in which high vacuums would be an impractical desorption method. According to the Union Carbide charts, approximately 0.08 grams/gram of adsorbent (g/g Ads.) remains on molecular sieves at 160° C. and 1 Atm pressure.

Neither the Union Carbide data nor our data indicate a significant preferential adsorption. There is some indication that less propylene is desorbed at lower temperatures with larger amounts desorbing at higher temperatures.

Adsorption of a propane-propylene mixture was tested by allowing a 0.5 mol fraction propylene, 0.5 mol fraction propane mixture (49 and 51% by weight) to flow through a previously used and desorbed column (160° C., 1 Atm). For adsorption, the column was at 27° C. At first, a high concentration of propane flowed out of the column until gradual breakthrough of propylene occurred and the outlet concentration was essentially equal to inflow concentration. This indicated equilibrium of the adsorbent with the entering gas composition at 1 Atm pressure and 27° C.

Variable temperature desorption was carried out by heating the column to 50° C. and as the gases were desorbed, they were released from the adsorbent column to an evacuated chamber for measurement by pressure, volume, and temperature. The adsorbent column waS maintained at 1 Atm pressure by releasing gas until the pressure remained constant indicating the complete desorption at this temperature. The gas desorbed was sampled for gas chromatography analysis. The column was then heated to 80° C. and 1 Atm pressure and the quantity and composition of the desorbed gas was measured as before. This procedure was repeated at 100°, 120°, 140° and 160° C., all at 1 Atm pressure, with quantity and composition measurements for desorbed gases. The column and tubing were of a minimal volume to reduce the effect of gases in the system, and the gases measured were the total gases leaving the column and tubing.

The results of the variable temperature desorption are shown in Table VII. In spite of the similar properties of propane and propylene and the fact that similar adsorptivities and desorption were obtained with pure components, there was a preferential adsorption of propylene when the mixture was adsorbed, and from a 49, 51% propylene, propane mixture, the concentration of the total amount adsorbed and desorbed was 82.1% propylene (by weight). This was apparent, but not measured, from the outflow of the column during adsorption.

The application of the principles of this invention, the desorption at various temperatures, gave a mixture of 74.7% propylene desorbing at up to 100° C., and a mixture of 91.3% propylene desorbing from 100° C. to 160° C. This is a significant increase from the 82.1% propylene that would have been obtained by complete desorption. Since propylene and propane are generally found or produced together and separation of these two components is difficult and costly by commercial distillation methods, the additional separation obtained by the application of this invention to an adsorption separation is quite significant.

TABLE VI

ADSORPTION OF PURE PROPANE AND PROPYLENE ON MOLECULAR SIEVES 5A
A. Data supplied by Union Carbide
Total Propane adsorbed at 1 Atm and 25° C., 0.10 g/g Adsorbent
Total Propylene adsorbed at 1 Atm and 25° C., 0.11 g/g Adsorbent
B. Adsorbed at 27° C. and 1 Atm onto previously used adsorbent, previously desorbed at 160° C. and 1 Atm, and measured by desorption.

|  | Propane g/g Adsorbent | Propylene g/g Adsorbent |
|---|---|---|
| Desorbed 50° C. | 0.00712 | .00360 |
| Desorbed 50° C. to 80° C. | 0.00485 | .00692 |
| Desorbed 80° C. to 100° C. | 0.00418 | .00415 |
| Desorbed 100° C. to 120° C. | 0.00444 | .00387 |
| Desorbed 100° C. to 140° C. | 0.00464 | .00471 |
| Desorbed 140° C. to 160° C. | 0.00493 | .00498 |
| Total Desorbed | 0.03016 | .02823 |

TABLE VII

DESORPTION OF PROPANE AND PROPYLENE FROM MOLECULAR SIEVES 5A AFTER ADSORPTION OF 49 WEIGHT % PROPYLENE 51% PROPANE AT 1 ATM AND 27° C.

|  | Total Desorbed g/g M. Sieves | Wt. Fraction Propylene | Wt. Propylene Desorbed g/g M.S. | Wt. Propane Desorbed g/g M.S. |
|---|---|---|---|---|
| Desorbed 50° C. | .00325 | .625 | .00203 | .00122 |
| Desorbed 50° C. to 80° C. | .00576 | .769 | .00443 | .00133 |
| Desorbed 80° C. to 100° C. | .00322 | .829 | .00267 | .00055 |
| Total to 100° C. | .01223 | .747 | .00913 | .00310 |
| Desorbed 100 to 120° C. | .00430 | .854 | .00367 | .00063 |
| Desorbed 120 to 140° C. | .00420 | .914 | .00384 | .00036 |
| Desorbed 140 to 160° C. | .00568 | .958 | .00544 | .00024 |
| Total Desorbed 100° C. to 160° C. | .01418 | .913 | .01295 | .00123 |
| Total Desorbed | .02641 | .821 | .02208 | .00433 |

EXAMPLE 4

ADSORPTION-DESORPTION SEPARATIONS FOR $CO_2$ PROPANE AND $H_2S$ ON MOLECULAR SIEVES (13X)

Adsorption Step

Adsorption of a $C_3H_8$—$CO_2$—$H_2S$ mixture was tested by allowing a mixture of 50 mol % $C_3H_8$, 25 mol % $CO_2$ and 25 mol % $H_2S$ to flow through an adsorbent column which contained approximately 15 g of molecular sieves (13X). For adsorption, the column was at 24° C., and the gas mixture was passed through the column into a chamber that was used to measure the quantity of gas leaving the column. This chamber was alternately evacuated and filled to atmospheric pressure with the column outflow. From volume, pressure, and temperature, the outflowing number of mols were calculated, and samples of each filling were analyzed. Equilibrium of the adsorbent with the gas mixture was assumed when the outflow was essentially equal in composition with the inflow and, after isolating, the pressure remained constant at 1 atmosphere and 24° C.

Desorption Step

The gas mixture was desorbed by heating the adsorbent column, first to 51° C., and later to higher temperatures. The gas desorbed after heating was released from the column to an evacuated chamber for measurement by pressure, volume and temperature. Gas was released until there was no change in the atmospheric pressure of the column, at a given temperature. This indicated the complete desorption at this temperature. The desorbed gas was sampled for gas chromatography analysis. The column was then heated to 80° C. and the quantity and composition of the desorbed gas was measured as before. This procedure was repeated at various steps in temperature up to 162° C. At each temperature, the pressures of the column and of the chambe were recorded for quantity measurements, and after each desorption temperature and chamber was evacuated by the vacuum pump.

For the adsorption equilibria of $CO_2$ and $H_2S$ on 13X molecular sieves, Union Carbide charts indicate the following with extrapolation:

| At 1 Atmosphere and Temperature | Equilibrium For Pure $CO_2$ | Equilibrium For pure $H_2S$ |
|---|---|---|
| −25° C. | 4.75 mg mol/g | |
| 25° C. | | 5.85 mg mol/g |
| 150° C. | | 2.88 mg mol/g |

This data indicates that $H_2S$ is adsorbed to a greater extent than $CO_2$ on this adsorbent. It also indicates high temperatures are needed to remove $H_2S$ from the adsorbent. It is not clear what $CO_2$ adsorptivities are in this range, nor how they are affected by temperatures. Judging from the adsorptivity of $H_2S$ at 150° C., it seems likely that the concentration of desorbed gas would be higher in $H_2S$ at the higher temperatures.

The results of the variable temperature desorption are shown in Table VIII. There was an obvious preferential adsorption of $H_2S$ and of $CO_2$ compared to propane when the mixture of 50% $C_3H_8$—25% $H_2S$—25% $CO_2$ was adsorbed. The application of the principles of this invention, the desorption at various temperatures, gave a mixture of 56.1% $H_2S$ desorbing at up to 125° C. and a mixture of 93.9% $H_2S$ desorbing from 125° C. to 165° C. This is a significant increase from the 78% $H_2S$ that would have been obtained by complete desorption. Otherwise, this process gave a mixture of 29.1% $C_3H_8$ and 14.7% $CO_2$ desorbing at up to 125° C., and a mixture of 2.7% $C_3H_8$ and 3.4% $CO_2$ desorbing from 125° C. to 165° C. This type of procedure could have a significant benefit in separating $H_2S$ from petroleum or natural gas and for separating $H_2S$ from $CO_2$. Its application could be useful as a pretreatment prior to a sulfur process to convert $H_2S$ to sulfur or as a method of treating tail gases from a sulfur plant for recycling. It could be of benefit in any process where it is desired to separate $H_2S$ from either hydrocarbons or $CO_2$.

In this example, propane was used as a typical hydrocarbon gas. Similar results would be expected with other natural gas or petroleum hydrocarbons.

TABLE VIII

THE RESULTS OF DESORPTION STEP FOR $C_3H_8$—$H_2S$—$CO_2$ MIXTURE ON MOLECULAR SIEVE ADSORBENT (13X)

| Run No. | T (°C.) | Component | Mole Fraction | No. mg Moles | Total Moles |
|---|---|---|---|---|---|
| 1 | 42 | $C_3H_8$ | .711 | 1.237 | |
| | | $H_2S$ | .092 | .160 | 1.74 |
| | | $CO_2$ | .197 | .343 | |
| 2 | 51 | $C_3H_8$ | .406 | .378 | |
| | | $H_2S$ | .480 | .446 | 0.93 |
| | | $CO_2$ | .114 | .106 | |
| 3 | 80 | $C_3H_8$ | .255 | .493 | |
| | | $H_2S$ | .606 | 1.170 | 1.93 |
| | | $CO_2$ | .138 | .267 | |
| 4 | 103 | $C_3H_8$ | .139 | .268 | |
| | | $H_2S$ | .721 | 1.392 | 1.93 |
| | | $CO_2$ | .140 | .271 | |
| 5 | 125 | $C_3H_8$ | .096 | .233 | |
| | | $H_2S$ | .766 | 1.862 | 2.43 |
| | | $CO_2$ | .138 | .335 | |
| Total From First 5 Steps 42° C. to 125° C. | | $C_3H_8$ | .291 | 2.609 | |
| | | $H_2S$ | .561 | 5.031 | 8.961 |
| | | $CO_2$ | .147 | 1.321 | |
| 6 | 154 | $C_3H_8$ | .037 | .111 | |
| | | $H_2S$ | .887 | 2.661 | 3.0 |
| | | $CO_2$ | .076 | .227 | |
| 7 | 164 | $C_3H_8$ | .023 | .062 | |
| | | $H_2S$ | .955 | 2.559 | 2.68 |
| | | $CO_2$ | .022 | .059 | |
| 8 | 165 | $C_3H_8$ | .024 | .060 | |
| | | $H_2S$ | .951 | 2.425 | 2.55 |
| | | $CO_2$ | .025 | .064 | |
| 9 | 160 | $C_3H_8$ | .026 | .052 | |
| | | $H_2S$ | .955 | 1.892 | 1.98 |
| | | $CO_2$ | .019 | .037 | |
| 10 | 162 | $C_3H_8$ | .02 | .036 | |
| | | $H_2S$ | .965 | 1.766 | 1.83 |
| | | $CO_2$ | .015 | .027 | |
| Total From Last 5 Steps 125° C. to 162° C. | | $C_3H_8$ | .027 | .321 | |
| | | $H_2S$ | .939 | 11.303 | 12.04 |
| | | $CO_2$ | .034 | .441 | |
| Total from All 10 Steps | | $C_3H_8$ | .14 | 2.93 | |
| | | $H_2S$ | .78 | 16.33 | 21.0 |
| | | $CO_2$ | .08 | 1.74 | |

EXAMPLE 5

DESORPTION FROM A SOLID TO A LIQUID

Desorption, or elution, of adsorbed components into a liquid solution is much less sensitive to temperature than desorption into a gas, because of the low energy requirements from solid to liquid compared to energy requirements from solid to gas. However, differences exist which may be utilized to partially separate components by variable temperature desorption. These methods could be useful in separating components which do not vaporize or which decompose or are degraded at higher temperatures.

A study of the desorption of ethanol and isopropanol into liquid water was made by first adsorbing ethanol and isopropanol from a water solution of 22% isopropanol and 23% ethanol by weight onto activated carbon (Calgon F200). This was done on 6 samples, designated C through H, at room temperature (24° C.) and a ratio of 5 ml of liquid per g of carbon. Liquids were decanted and the carbon was washed rapidly twice with 10 ml of water, to reduce ethanol and isopropanol in the undecanted surface water on the carbon. The samples were then desorbed in various ways at either room temperature or 65° C.

Sample C was desorbed 2 hours in 4 g of water per g of carbon at room temperature while sample D was desorbed the same way at 65° C. In the resulting decanted liquids, the ratio of isopropanol to ethanol was 0.90 for the room temperature desorption and 1.01 for the desorption at 65° C. This indicated that higher temperatures increase the desorption of isopropanol compared to ethanol.

Samples E and F were each desorbed 2 hours into 2 g of water per g of carbon at 24° C. and the average ratio of isopropanol to ethanol in the solution decanted from the carbon was 1.08. Samples G and H were each desorbed in the same way at 65° C., and the ratio of desorbed isopropanol to ethanol was 1.37. This again indicates that higher temperatures increase the desorption of isopropanol compared to ethanol.

After the first desorption of samples E and F which involved identical treatments, sample E was desorbed a second time in 2 g of water per g of carbon at 24° C. while F was desorbed a second time at 65° C. Sample E produced a desorption ratio of isopropanol to ethanol of 0.93 while F gave a similar ratio of 1.01. This indicates that on a second desorption, isopropanol desorption is increased compared to ethanol at higher temperatures.

After the first desorption of samples G and H involving identical treatment, second desorption were carried out in the same way as on E and F, with G desorbed at 24° C. the second time and H desorbed at 65° C. In this case, the liquids from desorption had ratios of isopropanol to ethanol of 1.27 for G at 24° C. and 2.5 for H at 65° C. Again, higher ratios of isopropanol to ethanol were obtained at higher temperatures.

Even though isopropanol and ethanol are very similar in their physical and chemical properties, in all the above cases there was evidence that isopropanol desorption was increased compared to ethanol desorption at the higher temperatures. The differences obtained in this desorption into liquid water were smaller than differences obtained in the desorptions of other compounds into the gas phase. However, these results indicate that the use of variable temperature desorption does produce changes in desorption of some components compared to others. Such changes are likely to have useful applications in some separations. Such applications seem to be more likely in separations of nonvolatile components sensitive to thermal effects but not decomposed or degraded by moderate changes in temperature. This could include components of a biological nature.

In view of the above, it will be seen that the several objects of the invention are achieved and other advantageous results obtained.

As various changes could be made in the above methods without departing from the scope of the invention, it is intended that all matter contained in the above description shall be interpreted as illustrative and not in a limiting sense.

What is claimed:

1. A process for the separation of ethanol from an ethanol-water mixture comprising about 2 to about 50% ethanol by weight, the process comprising:
    charging the ethanol-water mixture to an inlet end of a bed of adsorbent material having a greater affinity for ethanol than for water,
    passing the mixture through the bed, and withdrawing an effluent from an outlet end of the bed, the effluent consisting essentially of the mixture decreased in content of the ethanol and water adsorbed by the bed,
    after the adsorbent material is substantially saturated, desorbing the ethanol and water from the adsorbent material in at least two steps at substantially the same pressure but at different temperatures, one of the steps being carried out at a temperature of about 45° C. to about 95° C. and a subsequent desorption step being carried out at a greater temperature than that of the first step and a temperature of about 75° C. to about 150° C., and
    separately recovering the material desorbed in the two steps, the concentration of water being greater in the material recovered from the first desorption step than in the material recovered from the subsequent desorption step and the concentration of ethanol being greater in the material recovered from the subsequent desorption step than in the material recovered from the first desorption step.

2. A process as set forth in claim 1, wherein the adsorbent material is activated charcoal or activated carbon 3. An adsorption-desorption process for separation of a component from a liquid feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising:
    vaporizing the liquid feed mixture,
    charging the vaporized feed mixture to an inlet end of a bed of the adsorbent material,
    passing the vaporized feed mixture through the bed under such conditions that the adsorbent material adsorbs said first and second components of the feed mixture,
    withdrawing an effluent from an outlet end of the bed, the effluent consisting essentially of vaporized feed material decreased in content of the materials adsorbed by the bed,
    after the adsorbent material is substantially saturated, desorbing the first and second components from the adsorbent material in at least two steps at substantially the same pressure but at different temperatures, the temperature of the first desorption step being less than the temperature of a subsequent desorption step, and
    separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

4. A process as set forth in claim 3 wherein said first and second components are desorbed into a gas phase in said first and subsequent desorption steps.

5. A process as set forth in claim 3 wherein said first and second components are desorbed into a stripper gas in said first and subsequent desorption steps.

6. A process as set forth in claim 3 wherein said desorption steps are carried out at atmospheric pressure.

7. A process as set forth in claim 3 wherein said first and second components are desorbed into a liquid phase in said first and subsequent desorption steps.

8. An adsorption-desorption process for separation of a component from a feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising:

charging the feed mixture to an inlet end of a bed of the adsorbent material, passing the feed mixture through the bed under such conditions that the adsorbent material adsorbs said first and second components of the feed mixture, withdrawing an effluent from an outlet end of the bed, the effluent consisting essentially of feed material decreased in content of the materials adsorbed by the bed, after the adsorbent material is substantially saturated, desorbing the first and second components from the adsorbent material in at least two steps at atmospheric pressure but at different temperatures, the temperature of the first desorption step being less than the temperature of a subsequent desorption step, and separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

9. An adsorption-desorption process for separation of a component from a liquid feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising:

charging the feed mixture to an inlet end of a bed of the adsorbent material, passing the feed mixture through the bed under such conditions that the adsorbent material absorbs said first and second components of the feed mixture, withdrawing an effluent from an outlet end of the bed, the effluent consisting essentially of feed material decreased in content of the materials adsorbed by the bed, after the adsorbent material is substantially saturated, desorbing the first and second components from the adsorbent material in at least two steps at substantially the same pressure but at different temperatures, the temperature of the first desorption step being less than the temperature of a subsequent desorption step, and separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

10. An adsorption-desorption process for separation of a component from a feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising:

charging the feed mixture to an inlet end of a bed of the adsorbent material, passing the feed mixture through the bed under such conditions that the adsorbent material adsorbs said first and second components of the feed mixture, withdrawing an effluent from an outlet end of the bed, the effluent consisting essentially of feed material decreased in content of the materials adsorbed by the bed, after the adsorbent material is substantially saturated, desorbing the first and second components from the adsorbent material into a liquid phase in at least two steps at substantially the same pressure but at different temperatures, the temperature of the first desorption step being less than the temperature of a subsequent desorption step, and separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

11. An adsorption-desorption process for separation of propylene from a propane-propylene feed mixture, the process comprising:

charging the feed mixture to an inlet end of a bed of an adsorbent material, passing the feed mixture through the bed under such conditions that the adsorbent material adsorbs propane and propylene from the feed mixture, withdrawing an effluent from an outlet end of the bed, the effluent consisting essentially of the mixture decreased in content of the propane and propylene adsorbed by the bed, after the adsorbent material is substantially saturated, desorbing the propane and propylene from the adsorbent material in at least two steps at different temperatures, the temperature of the first desorption step being less than the temperature of a subsequent desorption step, and separately recovering the material desorbed in said steps.

12. A process as set forth in claim 11 wherein said adsorbent is a molecular sieve.

13. An adsorption-desorption process for separation of the components of a propane-carbon dioxide-hydrogen sulfide feed mixture, the process comprising:

charging the feed mixture to an inlet end of a bed of an adsorbent material, wherein the adsorbent material has a greater affinity for a first one of said components than for a second one of said components, passing the feed mixture through the bed under such conditions that the adsorbent material adsorbs the components from the feed mixture, withdrawing an effluent from an outlet end of the bed, the effluent consisting essentially of the mixture decreased in content of the components from the feed mixture adsorbed by the bed, after the adsorbent material is substantially saturated, desorbing the adsorbed components from the adsorbent material in at least two steps at different temperatures, the temperature of the first desorption step being less than the temperature of a subsequent desorption step, and separately recovering the material desorbed in said steps.

14. A process as set forth in claim 13 wherein said mixture is propane-carbon dioxide-hydrogen sulfide mixture comprising about 20% to about 99% propane by weight, the adsorbent has a greater affinity for hydrogen sulfide than for propane and carbon dioxide, the first desorption step is carried out at a temperature of about 40° C. to about 130° C. and the second desorption step is carried out at a temperature of about 90° C. to about 170° C.

15. A process as set forth in claim 14 wherein said adsorbent is a molecular sieve.

16. An adsorption-desorption process for separation of a component from a feed mixture of components wherein at least two components of the feed mixture are adsorbed by an adsorbent material during the adsorption step of the adsorption-desorption process and the adsorbent material has a greater affinity for a first one of said adsorbed components than for a second one of the adsorbed components, the process comprising:

charging the feed mixture to an inlet end of a bed of the adsorbent material, passing the feed mixture through the bed under such conditions that the adsorbent material adsorbs said first and second components of the feed mixture, withdrawing an effluent from an outlet end of the bed, the effluent consisting essentially of feed material decreased in content of the materials adsorbed by the bed, after the adsorbent material is substantially saturated, desorbing the first and second components from the adsorbent material into a stripper gas in at least two steps at atmospheric pressure but at different temperatures, the temperature of the first desorption step being less than the temperature of a subsequent desorption step, and separately recovering the material desorbed in said steps, the concentration of said first component being greater in the material recovered from said subsequent desorption step than in the material recovered from said first desorption step, and the concentration of said second component being greater in the material recovered from the first desorption step than in the material recovered from said subsequent desorption step.

17. A process as set forth in claim 16, wherein said mixture is an ethanol-water mixture comprising about 2 to about 50% ethanol by weight, the adsorbent material has a greater affinity for ethanol than for water, said first and subsequent desorption steps are carried out at atmospheric pressure, the first desorption step is carried out at a temperature of about 45° C. to about 95° C. and the subsequent desorption step is carried out at a temperature of about 75° C. to about 150° C.

18. A process as set forth in claim 17 wherein the adsorbent material is activated charcoal or activated carbon.

19. A process as set forth in claim 16 wherein the component to be separated from the feed mixture of components is adsorbed by the adsorbent material along with at least two other components of said feed mixture, the adsorbent material has a greater affinity for said component to be separated than for at least one of the other two components of the feed mixture adsorbed by the adsorbent material, and the concentration of said component to be separated is greater in the material recovered from said subsequent desorption step than in the material recovered from said first desorption step, and the concentration of said one of the other two components is greater in the material recovered from the first desorption step than in the material recovered from said subsequent desorption step.

20. A process as set forth in claim 19 wherein said mixture is a hydrocarbon-carbon dioxide-hydrogen sulfide mixture.

* * * * *